US00PP29947P3

(12) United States Plant Patent
Suphachadiwong

(10) Patent No.: US PP29,947 P3
(45) Date of Patent: Dec. 4, 2018

(54) ***DENDROBIUM* PLANT NAMED 'SUDEN1603'**

(50) Latin Name: ***Dendrobium* hybrid Sw.**
Varietal Denomination: Suden1603

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/731,869

(22) Filed: Aug. 16, 2017

(65) Prior Publication Data

US 2018/0054940 P1 Feb. 22, 2018

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Dendrobium* cultivar named 'Suden1603' which is characterized by the combination of a small to medium plant size, medium-sized flowers, purple flowers with sepals that are tipped white, as well as the stability of these characteristics from generation to generation.

3 Drawing Sheets

Latin name of the genus and species: The Latin name of the genus and species of the novel variety disclosed herein is *Dendrobium* hybrid Sw.

Variety denomination: The inventive variety of *Dendrobium* disclosed herein has been given the variety denomination 'Suden1603'.

CROSS REFERENCE TO RELATED APPLICATIONS

This application claims priority to the Community Plant Variety Rights application number 2016/2011, filed Aug. 16, 2016, which is herein incorporated by reference.

BACKGROUND OF THE INVENTION

Parentage: The *Dendrobium* variety 'Suden1603' is the result of a planned breeding program. 'Suden1603' originated as a seedling from the crossing of *Dendrobium* 'B' (not patented), the seed parent, with *Dendrobium* 'J2No.1' (not patented), the pollen parent. Both parents were developed by, and are owned by, the inventor and were never commercially released. The crossing was made by the inventor in his research greenhouse in Bangphra, Thailand in October of 2002. The new variety was first selected in February of 2005 due its unique growth and bloom characteristics, in a research greenhouse in Bangphra, Thailand belonging to the inventor. After identifying the new variety as a potentially interesting selection, the inventor continued confidential testing and propagation of 'Suden1603', to confirm the stability and uniformity of the unique characteristics first observed.

Asexual Reproduction: Asexual reproduction of the new cultivar 'Suden1603', by way of mericloning, was first initiated in June of 2006 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through five subsequent generations, the unique features of this cultivar have proven to be stable and true to type.

SUMMARY OF THE INVENTION

The cultivar 'Suden1603' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Suden1603'. These characteristics in combination distinguish 'Suden1603' as a new and distinct *Dendrobium* cultivar:

1. *Dendrobium* 'Suden1603' exhibits a small to medium plant size; and
2. *Dendrobium* 'Suden1603' exhibits medium-sized flowers; and
3. *Dendrobium* 'Suden1603' exhibits a purple general tonality of the flower with the apices and distal portion of the sepals colored white.

BOTANICAL DESCRIPTION OF THE PLANT

Figure 1:
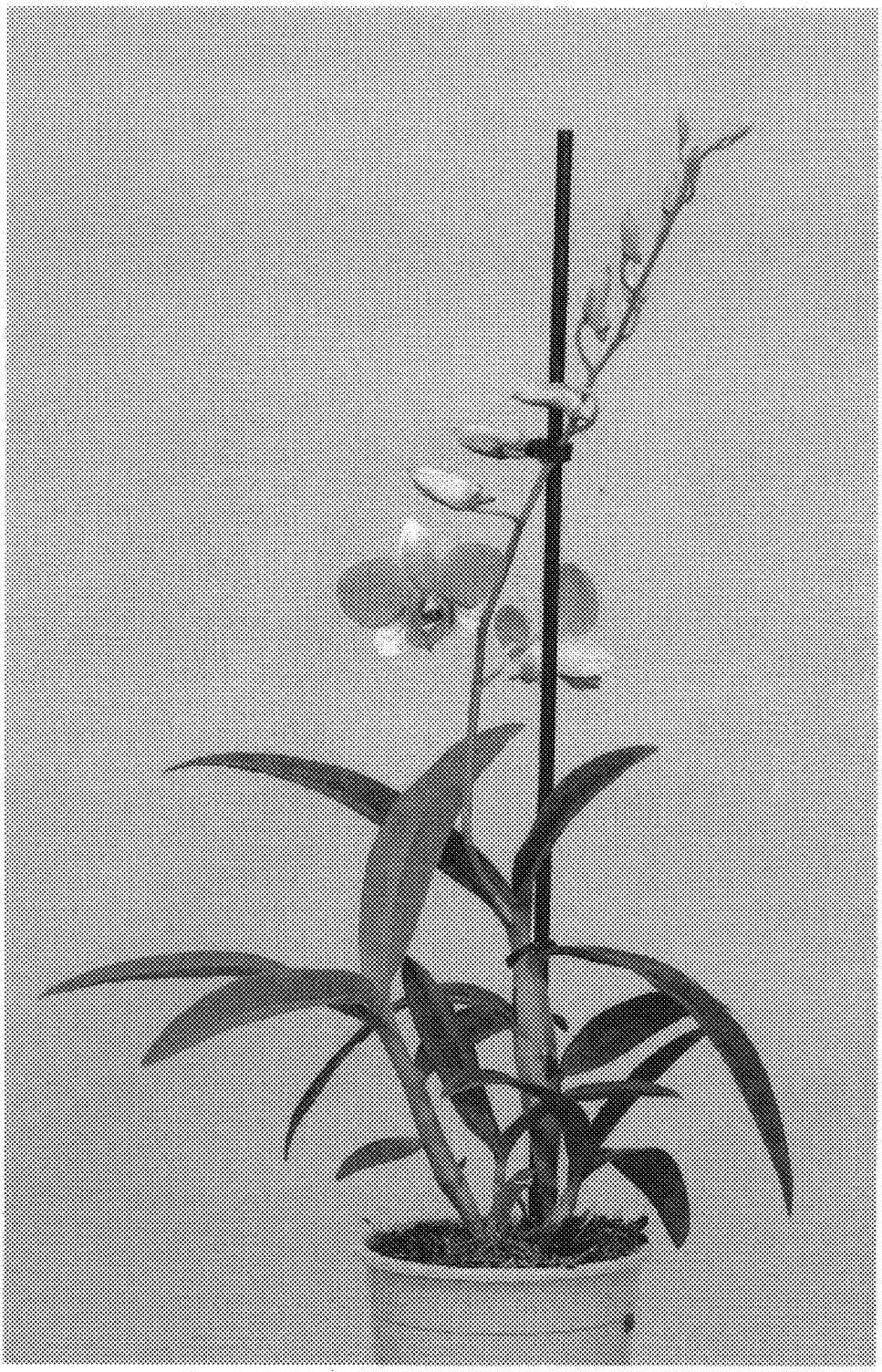
FIG. 1 illustrates, as nearly true as it is reasonably possible to make the same in color photographs of this type, an exemplary plant of 'Suden1603' grown in a commercial greenhouse in Honselersdijk, the Netherlands. This plant, grown in an 11 cm nursery container, is approximately 35 months old from a rooted young plant.
Figure 2:
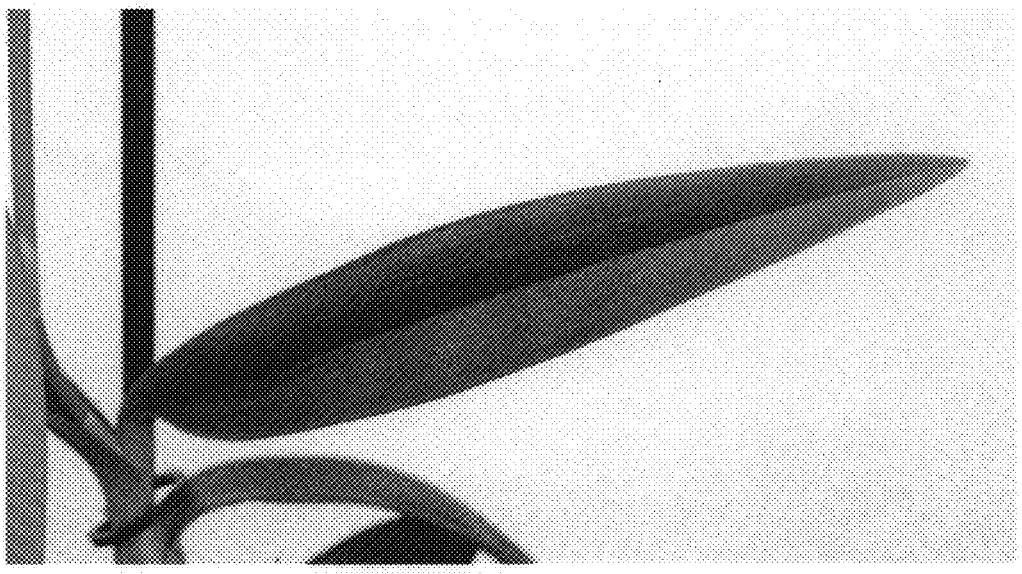
FIG. 2 illustrates, as nearly true as it is reasonably possible to make the same in color photographs of this type, the typical foliage of 'Suden1603'.
Figure 3:
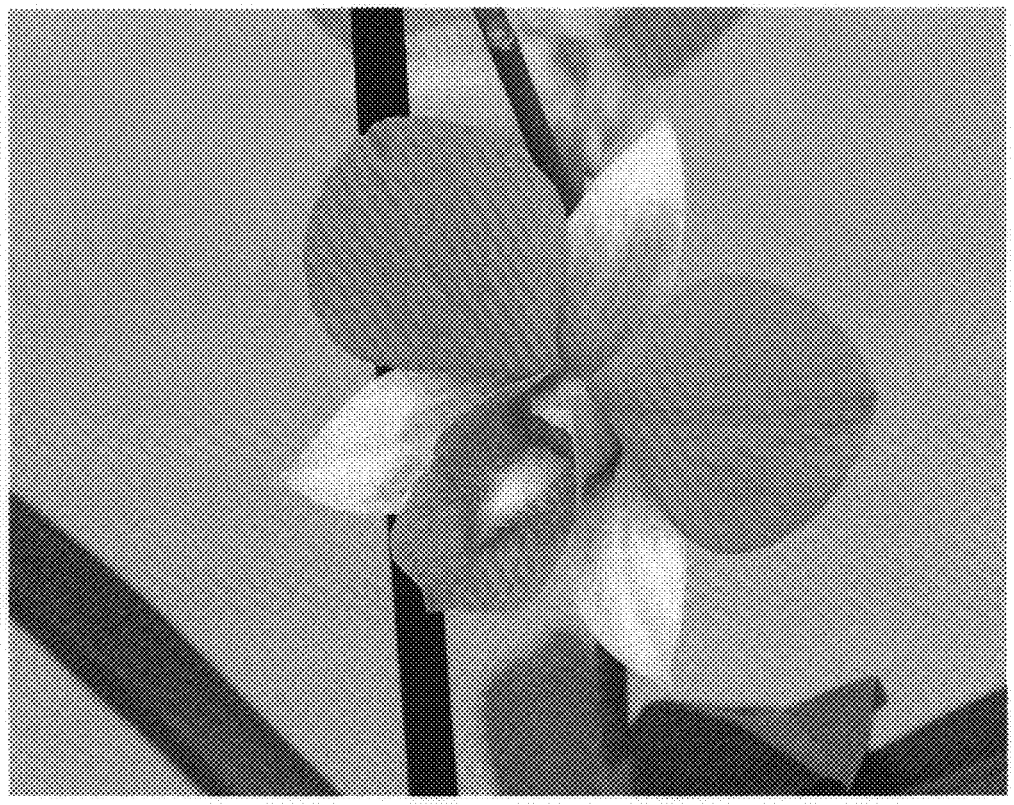
FIG. 3 illustrates, as nearly true as it is reasonably possible to make the same in color photographs of this type, the typical flowers of 'Suden1603'.

The following observations and measurements made in August of 2017 describe averages from a sample set of six specimens of 35 month-old 'Suden1603' plants grown in 11 cm nursery pots in a greenhouse in Bangphra, Thailand. Temperatures ranged from approximately 26 to 30 degrees Celsius. The light sum was set at 5 moles per day and the plant was given shading and artificial light in order to achieve the light sum of 5 moles per day.

Those skilled in the art will appreciate that certain characteristics will vary with older or, conversely, with younger plants. 'Suden1603' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'Suden1603' and comparisons with the parents and most similar commercial variety of *Dendrobium* are provided below.

Plant description:

*Growth habit.*—Perennial; sympodial, upright. Multiple leafy pseudobulbs growing from base, with flowers in terminal inflorescences, carried above the leaf plane.

*Average height from base (plant grown in hanging basket, so no soil line present) to top of foliage.*—18.1 cm.

*Average height from base (plant grown in hanging basket, so no soil line present) to top of flowers.*—41.2 cm.

*Plant spread.*—Average of 27.8 cm.

*Growth rate.*—Moderate.

*Plant vigor.*—Moderate.

*Propagation details.*—Tissue culture propagation is performed using meristem culture. Meristematic tissue is harvested from the center of a newly-emerged vegetative bud and grown on by constant agitation in a nutrient rich liquid until the cell mass is large enough to be split into small sections. These sections are either rooted and grown into young plants for finishing in nursery pots or the tissue culture process is repeated to produce more clones.

*Time to produce a marketable plant.*—Mericloning requires 18 months to yield a propagule which is ready to be rooted, or "deflasked", in soilless propagation media. After deflasking the micropropagule, an additional 9 to 12 months is required to produce a fully rooted plant under average temperatures ranging between 26 and 30 degrees Celsius.

*Disease and pest resistance or susceptibility.*—Plants have not been observed to be susceptible or resistant to pathogens and pests common to *Dendrobium*.

*Environmental tolerances.*—Adapt to at least USDA Zones 11 and 12 and temperatures as high as 40 degrees Celsius; high tolerance to rain; moderate tolerance to wind.

Root system:

*General.*—Moderately dense rooting.

*Dimensions, mature roots.*—7.1 cm long with a diameter of 0.25 cm, on average.

*Texture.*—Fleshy; non-fibrous.

*Color.*—White, nearest to RHS NN155A; older roots are orange-white, nearest to RHS 158B.

Stem:

*Branching habit.*—Sympodial; pseudobulbs growing from base; no lateral branches present.

*Number of primary (main) stems per plant.*—Four.

*Number of secondary (lateral) branches per plant.*—None.

*Longitudinal section shape.*—Narrow elliptic to oblanceolate; axially ribbed.

*Cross section shape.*—Elliptical.

*Length.*—10.7 cm.

*Diameter.*—Averaging 1.6 cm at the widest point and 1.5 cm at the narrowest point.

*Internode length.*—2.1 cm.

*Luster.*—Slightly glossy.

*Attitude.*—Average angle is 17.5 degrees from vertical plane; ranging from 5 to 30 degrees.

*Strength.*—Strong.

*Color, juvenile.*—Yellow-green, nearest to RHS 144A.

*Color, mature.*—Yellow-green, nearest to RHS 146A.

*Color at internodes.*—Yellow, nearest to in between RHS 5A and 5B.

*Color of older stem.*—Greyed-green, nearest to in between RHS 195B and 195C.

*Pubescence.*—Glabrous.

Foliage:

*Arrangement.*—Distichous.

*Quantity.*—Approximately 17 leaves per plant.

*Lamina.*—Dimensions — 14.9 cm long and 3.0 cm wide, on average. Shape — Lanceolate. Aspect — Very slightly curved. Apex — Acute. Base — Sheathing. Sheath dimensions — 3.0 cm long and 1.5 cm wide, on average. Sheath color — Yellow-Green, nearest to RHS 145B; veined darker, nearest to RHS 144B. Margin — Entire. Pubescence, texture and luster of adaxial surface — Glabrous, smooth, and moderately glossy. Pubescence, texture and luster of abaxial surface — Glabrous, smooth, and slightly glossy. Color — Juvenile foliage, adaxial surface — Nearest to in between green, RHS 143A, and yellow-green, RHS 144A. Juvenile foliage, abaxial surface — Yellow-green, nearest to RHS 144A. Mature foliage, adaxial surface — Green, nearest to RHS NN137A. Mature foliage, abaxial surface — Yellow-green, nearest to RHS 146A. Venation — Parallel. Venation color, adaxial surface — Green, nearest to RHS NN137A. Venation color, abaxial surface — Yellow-green, nearest to RHS 146A.

*Petiole.*—No petioles present, leaves sessile.

Inflorescence:

*Inflorescence arrangement.*—Simple terminal raceme with flowers borne along the peduncle.

*Natural flowering season.*—Autumn into winter.

*Time to flower.*—Approximately 10 months.

*Inflorescence quantity.*—One.

*Flowers per inflorescence.*—Average of 13; 2 open flowers and 11 buds.

*Inflorescence height.*—Approximately 24.3 cm (measured from base of lowest flower to top of upper flower).

*Inflorescence diameter.*—Approximately 10.8 cm.

*Peduncle.*—Dimensions — Approximately 30.4 cm long and 0.25 cm wide. Attitude — Approximately 25 degree angle to main stem. Strength — Strong. Texture and luster — Glabrous and moderately glossy. Color — Green, nearest to RHS 143B.

Bud:

*Length.*—Average of 3.3 cm.

*Diameter.*—Average of 1.5 cm.

*Shape.*—Obovate; curved.

*Pubescence, texture and luster.*—Glabrous, smooth and matte.

*Color.*—Yellow-green, nearest to a combination of RHS 145B and 145C; apex and main veins of immature sepals are darker, nearest to RHS 145A; upper surface is heavily suffused with purple, RHS N77B.

Flower:

*Flower type.*—Zygomorphic (orchidaceous), typical shape for the genus *Dendrobium.*

*Flowering habit.*—Moderately floriferous.

*Shape.*—Zygomorphic, single; consisting of three sepals and three petals, one of which is transformed into a labellum; the two lateral petals are slightly overlapping the lateral sepals and dorsal sepal at the base of the petals.

*Aspect.*—Flowers are outward-facing.

*Height.*—Approximately 6.0 cm.

*Diameter.*—Approximately 6.4 cm.

*Depth.*—Approximately 3.3 cm.

*Fragrance.*—No fragrance.

*Lastingness.*—Up to 3 weeks.

*Persistent.*—Self-cleaning.

*Petals.*—Quantity of Petals — 3; two conventional petals and one labellum. Arrangement — One lateral petal on each side, separated by the labellum; unfused. Aspect — Petals are slightly folded inward and curled downward at the distal end. Length — Approximately 3.9 cm. Width — Approximately 3.0 cm. Shape — Broad rhomboidal to broad obovate; slightly curled backwards. Apex — Undeeply emarginate. Base — Cuneate. Margin — Entire; no undulation. Pubescence, texture and luster of upper surface — Glabrous, velvety and matte. Pubescence, texture and luster of lower surface — Glabrous, velvety and matte. Color when opening, upper surface — Purple, nearest to RHS NN78A, and veined slightly darker, nearest to RHS N78A. Color when opening, lower surface — Purple, nearest to RHS N78B; main vein is purple-violet, nearest to RHS N80C. Color when fully opened, upper surface — Purple, nearest to RHS NN78A. Color when fully opened, lower surface — In between purple, RHS N78B, and purple-violet, RHS N80B. Fading, upper surface — Not fading. Fading, lower surface — Not fading. Venation color, fully opened, upper surface — Purple, very slightly darker than RHS NN78A. Venation color, fully opened, lower surface — Main vein is purple-violet, nearest to RHS N80D. No other veins are visible.

*Labellum.*—Shape — Central lobe — Obovate. Lateral lobes — Obovate. Length — Central lobe — Approximately 3.3 cm. Lateral lobes — Approximately 2.0 cm. Width — Central lobe — Approximately 1.8 cm. Lateral lobes — Approximately 1.5 cm. Apex — Central lobe — Abruptly acute. Lateral lobes — Obtuse. Base — Central lobe — Cuneate. Lateral lobes — Cuneate. Aspect — Central lobe — Strongly concaved. Lateral lobes — Strongly concaved. Margin — Central lobe — Entire; not undulate. Lateral lobes — Entire; strongly undulate. Texture and luster of upper surface — Central lobe — Glabrous, velvety, and slightly glossy. Lateral lobes — Glabrous, velvety, and slightly glossy. Texture and luster of lower surface — Central lobe — Glabrous, slightly velvety, and moderately glossy. Lateral lobes — Glabrous, slightly velvety, and moderately glossy. Color when opening, upper surface — Central lobe — Purple, nearest to RHS N78A, with a slightly darker margin of the callosities, nearest to RHS N79C. Lateral lobes — Purple, nearest to a combination of RHS N78B and N78C, and fading to yellow-green towards the base, nearest to RHS 145D. Color when opening, lower surface — Central lobe — Purple-violet, nearest to RHS N80B, and fading to green-white towards the base, nearest to a combination of RHS 157B and 157C. Lateral lobes — Purple-violet, nearest to RHS N80B, and fading to greyed-white towards the base, nearest to in between RHS 156C and 157C. Color when fully opened, upper surface — Central lobe — Purple, nearest to in between RHS N78A and NN78A with a slightly darker apex and margins of the callosities, nearest to RHS NN78A. Lateral lobes — Purple, nearest to RHS N78C, and fading to yellow-green towards the base, nearest to RHS 145D. Color when fully opened, lower surface — Central lobe — Purple-violet, nearest to RHS N80B, and fading to green-white towards the base, nearest to a combination of RHS 157B and 157C. Lateral lobes — Purple-violet, nearest to in between RHS N80B and N80C, and fading to greyed-white towards the base, nearest to in between RHS 156B and 156C. Fading, upper surface — Not fading. Fading, lower surface — Not fading. Venation color, fully opened, upper surface — Central lobe — No veins are visible. Lateral lobes — No veins are visible. Venation color, fully opened, lower surface — Central lobe — Main vein is purple, nearest to RHS N78B; no other veins are visible. Lateral lobes — Main vein is purple, nearest to RHS N78B; no other veins are visible. Labellum eye — Not present. Callosities — Location — Centrally placed on the central lobe of the labellum. Length — 2.0 cm, on average. Width — 0.5 cm, on average. Color — Yellow-green, nearest to RHS 145C.

*Spurs.*—Quantity — Average of 1. Length — Approximately 0.8 cm. Diameter — Approximately 0.6 cm. Vertical height — Approximately 0.7 cm. Shape — Near triangular. Apex — Bluntly acute. Base — Broad Cuneate. Pubescence, texture and luster — Glabrous, smooth, and glossy. Color — Yellow-green, nearest to RHS 145C; apex and under side are purple, nearest to RHS NN78D.

*Sepals.*—Quantity — Average of 3 unfused sepals. Arrangement — One dorsal sepal and two lateral sepals. Length — Dorsal sepal — Approximately 3.5 cm. Lateral sepals — Approximately 3.5 cm. Width — Dorsal sepal — Approximately 1.4 cm. Lateral sepals — Approximately 1.7 cm. Shape — Dorsal sepal — Narrow ovate; slightly curled backwards. Lateral sepals — Ovate; slightly curled downward and slightly curled backwards. Apex — Dorsal sepal — Acute. Lateral sepals — Short apiculate. Base — Dorsal sepal — Broad cuneate. Lateral sepals — Broad cuneate. Margin — Dorsal sepal — Entire; not undulate. Lateral sepals — Entire; not undulate. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, moderately velvety, and matte. Lateral sepals — Glabrous, moderately velvety, and matte; slightly glossy at the base. Color when opening, upper surface — Dorsal sepal — Purple, nearest to in between RHS N78B and NN78D; apex is yellow-green, nearest to RHS 145B. Lateral sepals — Yellow-green, nearest to RHS 145C; apex is darker, nearest to a combination of RHS 145A and 145B; upper surface is purple, nearest to a combination of RHS N78A and N78B; lower surface is suffused with purple, nearest to RHS N78C. Color when opening, lower surface — Dorsal sepal — Purple, nearest to in between RHS 77B and 77C, and fading to yellow-green towards the apex, nearest to RHS 145B. Lateral sepals — Yellow-green, nearest to a combination of RHS 145B and 145C; apex is darker, nearest to RHS 145A; upper surface is suffused with purple, nearest to a combination of RHS N78C. Color when fully opened, upper surface — Dorsal sepal — Purple, nearest to in between RHS N78B and NN78C, and fading to green-white towards the apex, nearest to RHS 157B. Lateral sepals — Green-white, nearest to RHS 157D; apex is darker, nearest to RHS 157B; upper surface is purple, nearest to RHS NN78C; lower surface is suffused with purple, nearest to RHS N78C. Color when fully opened, lower surface — Dorsal sepal — Purple, nearest to a combination of RHS 77C and 77D, and fading to yellow-green towards the apex, nearest to RHS 145C. Lateral sepals — Yellow-green, nearest to RHS 145C; apex is darker, nearest to RHS 145B; upper surface is suffused with purple, nearest to RHS N78C; lower surface is suffused with purple, nearest to RHS 76C. Fading, upper surface — Not fading. Fading, lower surface — Not fading. Venation color, fully opened, upper surface — Dorsal sepal — No veins are visible. Lateral sepals — Main vein is yellow-green, nearest to RHS 145D; no other veins are visible. Venation color, fully opened, lower surface — Dorsal sepal — No veins are visible. Lateral sepals — No veins are visible.

*Pedicels.*—Length — Approximately 3.3 cm. Diameter — Approximately 0.2 cm. Angle — Approximately 70 degree angle to peduncle axis; varying between 60 and 90 degrees. Strength — Moderately strong. Texture and luster — Glabrous and moderately glossy. Color — Yellow-green, nearest to RHS 144B, and fading to green towards the proximal end, nearest to RHS 143A; suffused with purple towards the distal end, nearest to RHS N78B.

*Bract.*—Quantity — One bract present at the base of each pedicel. Shape — Ovate. Dimensions — Average of 0.7 cm long and 0.5 cm wide. Apex — Acute. Base — Folded around the base of the pedicel. Margins — Entire. Color, both surfaces — Yellow-green, nearest to RHS 145C; main vein and apex is darker, nearest to RHS 145B.

Reproductive organs:

*Column.*—Length — Approximately 0.6 cm. Diameter — Approximately 0.8 cm. Color — Yellow-green, nearest to RHS 145C, and margined purple, nearest to a combination of RHS N80A and N80B.

*Ovary.*—Position — Inferior Diameter — Approximately 0.25 cm. Color — Yellow-green, nearest to RHS N144B, and suffused with purple, nearest to RHS N78B.

*Pollinia color.*—Yellow, nearest to a combination of RHS 13B and 13C.

Seed and fruit: No fruit and seed production has been detected to date.

Comparisons with the parent plants: Plants of the new cultivar 'Suden1603' may be distinguished from its seed parent, *Dendrobium* 'B', by the characteristics described in Chart 1.

CHART 1

| Characteristic | 'Suden1603' | Dendrobium 'B' |
|---|---|---|
| Mature plant height. | Shorter than 'B'. | Taller than 'Suden1603'. |
| Bloom habit. | More floriferous than 'B'. | Less floriferous than 'Suden1603'. |
| Flower size. | Smaller than 'B'. | Larger than 'Suden1603'. |
| General coloration of the flower. | Purple, with sepals that are tipped white. | White. |

Plants of the new cultivar 'Suden1603' may be distinguished from its pollen parent, *Dendrobium* 'J2No.1', by the characteristics described in Chart 2.

CHART 2

| Characteristic | 'Suden1603' | 'J2No.1' |
|---|---|---|
| Plant vigor. | More vigorous than 'J2No.1'. | Less vigorous than 'Suden1603'. |
| Mature plant size. | Larger than 'J2No.1' | Smaller than 'Suden1603'. |
| Bloom habit. | More flowers per inflorescence compared to 'J2No.1'. | Fewer flowers per inflorescence compared to 'Suden1603'. |
| General coloration of the flower. | Darker purple. | Lighter purple. |

Comparison with the most similar *Dendrobium* cultivar known to the inventor: 'Suden1603' is similar in many horticultural characteristics to the commercial variety *Dendrobium* 'SPCDW1007 ' (U.S. Plant Pat. No. 26,324). However 'Suden1603' may be distinguished from 'SPCDW1007' by the characteristics described in Chart 3.

CHART 3

| Characteristic | 'Suden1603' | 'SPCDW1007' |
|---|---|---|
| Mature plant height. | Shorter than 'SPCDW1007'. | Taller than 'Suden1603'. |

CHART 3-continued

| Characteristic | 'Suden1603' | 'SPCDW1007' |
|---|---|---|
| General coloration of the petals. | Purple with dark purple veins. | Dark purple with dark purple veins. |
| General coloration of the sepals. | Cream to beige, suffused with purple; purple veins, | Dark purple with dark purple veins. |

That which is claimed is:

1. A new and distinct variety of *Dendrobium* plant named 'Suden1603', substantially as described and illustrated herein.

* * * * *